(12) United States Patent
Kim et al.

(10) Patent No.: US 8,771,743 B2
(45) Date of Patent: Jul. 8, 2014

(54) MULTI-LAYERED LAMELLAR GRANULE AND SKIN EXTERNAL APPLICATION COMPOSITION CONTAINING SAME

(75) Inventors: Do Hoon Kim, Seoul (KR); Eun Jung An, Paju-si (KR); Jae Sung Hwang, Seoul (KR); Hong Ju Shin, Seongnam-si (KR); Won Seok Park, Seoul (KR); Chang Geun Yi, Yongin-si (KR); Jong Hee Park, Yongin-si (KR); Jeong Hwan Kim, Paju-si (KR); Jin Woong Kim, Yongin-si (KR); Jung A Seo, Yongin-si (KR); Yong Jin Kim, Suwon-si (KR); Jong Won Shim, Yongin-si (KR); Mi Jin Kim, Goyang-si (KR)

(73) Assignee: Amorepacific Corporation, Seoul (KR)

( * ) Notice: Subject to any disclaimer, the term of this patent is extended or adjusted under 35 U.S.C. 154(b) by 76 days.

(21) Appl. No.: 13/055,091

(22) PCT Filed: Sep. 2, 2008

(86) PCT No.: PCT/KR2008/005143
§ 371 (c)(1),
(2), (4) Date: Jan. 20, 2011

(87) PCT Pub. No.: WO2010/010985
PCT Pub. Date: Jan. 28, 2010

(65) Prior Publication Data
US 2011/0123583 A1     May 26, 2011

(30) Foreign Application Priority Data

Jul. 24, 2008 (KR) .................. 10-2008-0072355
Aug. 29, 2008 (KR) .................. 10-2008-0085030

(51) Int. Cl.
*A61K 8/68* (2006.01)
*A61K 9/16* (2006.01)

(52) U.S. Cl.
USPC .......................... 424/489; 424/401

(58) Field of Classification Search
USPC ........................................ 424/401
See application file for complete search history.

(56) References Cited

U.S. PATENT DOCUMENTS

| 5,496,565 A | 3/1996 | Heinze et al. |
| 5,817,334 A * | 10/1998 | Schmidt et al. ............... 424/450 |

(Continued)

FOREIGN PATENT DOCUMENTS

| JP | 06-178930 A | 6/1994 |
| JP | 06-298638 A | 10/1994 |

(Continued)

OTHER PUBLICATIONS

European Patent Office, European Search Report issued in corresponding EP Application No. 08811636.3, dated Jul. 10, 2012.

(Continued)

*Primary Examiner* — Rachael E Bredefeld
(74) *Attorney, Agent, or Firm* — Sughre Mion, PLLC (57) ABSTRACT

Provided are: a multi-layered lamellar granule comprising a nucleating agent, a ceramide-containing artificial stratum corneum lipid lamellar layer which encases the nucleating agent and a polymer layer disposed on the artificial stratum corneum lipid lamellar layer; and an external skin application composition comprising the same. The external skin application composition shows improved moisturizing and barrier repair capabilities when applied to the skin, which can be advantageously used in cosmetics and pharmaceuticals.

19 Claims, 6 Drawing Sheets
(3 of 6 Drawing Sheet(s) Filed in Color)

(56) References Cited

U.S. PATENT DOCUMENTS

| | | | |
|---|---|---|---|
| 6,387,398 B1 * | 5/2002 | Vollhardt et al. | 424/450 |
| 6,761,901 B1 | 7/2004 | Betageri et al. | |
| 7,169,382 B2 | 1/2007 | Chopart et al. | |
| 2003/0113368 A1 * | 6/2003 | Nomoto et al. | 424/450 |
| 2004/0130968 A1 * | 7/2004 | Bach et al. | 366/348 |
| 2007/0082042 A1 * | 4/2007 | Park et al. | 424/450 |

FOREIGN PATENT DOCUMENTS

| | | |
|---|---|---|
| JP | 08-507765 A | 8/1996 |
| JP | 2001-48721 A | 2/2001 |
| JP | 2001-316384 A | 11/2001 |
| JP | 2002-536316 A | 10/2002 |
| JP | 2003-24767 A | 1/2003 |
| JP | 2008-520630 A | 6/2006 |
| JP | 2006-527265 A | 11/2006 |
| KR | 10-2007-0113711 A | 11/2007 |
| WO | 2006/053912 A1 | 5/2006 |
| WO | WO 2006/053912 * 5/2006 ............... A61K 8/68 |
| WO | 2007/004300 A1 | 1/2007 |

OTHER PUBLICATIONS

Japanese Patent Office, Japanese Office Action issued in corresponding JP Application No. 2011-519967, dated May 28, 2013.

\* cited by examiner

MULTI-LAYERED LAMELLAR GRANULE AND SKIN EXTERNAL APPLICATION COMPOSITION CONTAINING SAME

CROSS REFERENCE TO RELATED APPLICATION

This application is a National Stage of International Application No. PCT/KR2008/005143 filed Sep. 2, 2008, claiming priority based on Korean Patent Application No. 10-2008-0072355, filed Jul. 24, 2008 and Korean Patent Application No. 10-2008-0085030, filed Aug. 29, 2008, the contents of all of which are incorporated herein by reference in their entirety.

FIELD OF THE INVENTION

The present invention relates to a multi-layered lamellar granule comprising a ceramide-containing artificial stratum corneum lipid layer and an external skin application composition containing the same having improved epidermal moisturization and skin barrier repair capabilities.

BACKGROUND OF THE INVENTION

A ceramide is a sphingolipid composed of sphingosine and a fatty acid linked to sphingosine or phytosphingosine. A family of ceramides, which make up about 40% or more of the lipids present in cornified cells, is essential in controlling the structural organization and functions of the stratum corneum, among other vital physiological functions thereof.

Ceramides protect the skin from internal/external stresses, e.g., by removing disrupted cells, and they become depleted with advancing age. As a consequence, a number of detrimental factors such as the exposure to the external stimuli such as ultraviolet ray and chemicals cause water loss and the exfoliation of cornified cells, which causes the skin to become dry, cracked and fissured.

Such symptoms may be partially ameliorated by external application of ceramides. However, if a large amount of insoluble stratum corneum components are used in a cosmetic formulation, the amounts of additives such as emulsifiers and oils must be increased to enhance the solubility of the corneum components, which, however, results in the difficulty of forming a structure similar to the stratum corneum. Further, ceramides tend to aggregate and form a gel unsuitable for a cosmetic formulation, and therefore, its amount is generally limited to less than 1% by weight.

SUMMARY OF THE INVENTION

Accordingly, it is an object of the present invention to provide a multi-layered granule having improved formulation stability which comprises an artificial stratum corneum lipid lamellar layer similar to the skin stratum corneum.

It is another object of the present invention to provide an external application composition having improved cutaneous moisturization and barrier repair capabilities which comprises said multi-layered lamellar granule.

In accordance with an aspect of the present invention, there is provided a multi-layered lamellar granule comprising a nucleating agent, a ceramide-containing artificial stratum corneum lipid lamellar layer which encases the nucleating agent, and a polymer layer disposed on the artificial stratum corneum lipid lamellar layer.

In accordance with another aspect of the present invention, there is provided an external skin application composition comprising the multi-layered lamellar granule as disclosed above.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

The above and other objects and features of the present invention will become apparent from the following description of the invention, in conjunction with the following accompanying drawings, which respectively show.

DETAILED DESCRIPTION OF THE INVENTION

The present invention is described in detail hereinafter.

The present invention provides a multi-layered lamellar granule comprising a nucleating agent, a ceramide-containing artificial stratum corneum lipid lamellar layer which encases the nucleating agent, and a polymer overcoat layer disposed on the artificial stratum corneum lipid lamellar layer.

The nucleating agent used herein is an active colloid which disintegrates easily when an external stimulus is applied. Examples of the nucleating agent include sugar, a salt, hyaluronic acid, alginic acid, chondroitin sulfate, chitosan, chitin, polylysine, collagen, gelatin, stearic acid, cetyl alcohol, stearyl alcohol, and a mixture thereof.

Said nucleating agent may be used in an amount of 1 to 99% by weight based on the total amount of the multi-layered lamellar granule. When used in that amount, the coagulation of the corneum on coating decreases with increased coating efficiency.

The nucleating agent is embedded in an artificial stratum corneum lipid lamellar layer. The human stratum corneum layer is composed of keratinocytes and lipids located between the keratinocytes, which contributes to the skin barrier function. The lipids play a central role in manifesting the barrier function, and have a multi-layered lamellar structure. The artificial stratum corneum lipid lamellar layer mimics the human stratum corneum layer.

The artificial stratum corneum lipid lamellar layer comprises a ceramide as an essential constituent, and preferably further comprises a phospholipid, a fatty acid, a cholesterol or a derivative thereof, an alcohol, a molecular anchoring agent, or a mixture thereof.

The ceramide included in the artificial stratum corneum lipid lamellar layer is a natural ceramide or a pseudoceramide.

The natural ceramide may be selected from the group consisting of ceramide 1, ceramide 2, ceramide 3, ceramide 4, ceramide 5, ceramide 6, ceramide 7, ceramide 8, and a mixture thereof.

The pseudoceramide is a synthetic substance which is similar to a natural ceramide in terms of properties, e.g., skin protection and water retention capabilities, and it may be selected from the group consisting of the compounds of formulae (I) to (VI), and a mixture thereof.

(I)

(wherein,
R is a saturated or unsaturated $C_9$-$C_{21}$ aliphatic chain moiety);

(II)

(wherein,
n is 1 or 2; and
R and R' are each a saturated or unsaturated $C_9$-$C_{21}$ aliphatic chain moiety);

(III)

(wherein,
m and n are each independently an integer of 1 to 3;
k and l are each independently 1 or 2;
j is 0 or 1;
R and R' are each independently a linear or branched, saturated or unsaturated $C_1$-$C_{31}$ hydrocarbon group, optionally having one or more hydroxyl substituents; and
$A^1$, $A^2$ and $A^3$ are each independently hydrogen or one of following groups, with the proviso that $A^1$, $A^2$ and $A^3$ are not simultaneously hydrogen.

[wherein,
M, $M^1$ and $M^2$ are each independently selected from the group consisting of an alkali metal, a lysine moiety, an arginine moiety, a histidine moiety, triethylammonium, ammonium, polyquaternium-4, polyquaternium-6, polyquaternium-7, polyquaternium-10, polyquaternium-11, polyquaternium-16, lauryldimethylbenzylammoniumchloride and stearyldimethylbenzylammoniumchloride, and L is an alkali earth metal.]);

(IV)

(wherein,
R and R' are each independently a linear or branched, saturated or unsaturated $C_{10}$-$C_{32}$ hydrocarbon group, optionally having one or more hydroxyl substituents;
$R^3$ and $R^4$ are each independently hydrogen, $C_1$-$C_4$ alkyl, or $C_1$-$C_4$ hydroxyl alkyl; and
$R^5$ is -A or —$CH_2CH_2OA$, wherein A is one of following groups;

[wherein,

M, $M^1$ and $M^2$ are each independently selected from the group consisting of an alkali metal, a lysine moiety, an arginine moiety, a histidine moiety, triethylammonium, ammonium, polyquaternium-4, polyquaternium-6, polyquaternium-7, polyquaternium-10, polyquaternium-11, polyquaternium-16, lauryldimethylbenzylammoniumchloride and stearyldimethylbenzylammoniumchloride, and L is an alkali earth metal.]);

(V)

(Wherein, m and n are each independently an integer of 1 to 4;

R and R' are each independently a linear or branched, saturated or unsaturated $C_1$-$C_{31}$ hydrocarbon group, optionally having one or more hydroxyl substituents;

$A_1$ and $A_2$ are each independently hydrogen or one of following groups:

[wherein,

M, $M^1$ and $M^2$ are each independently an alkali metal or a nitrogen-containing organic base, and L is an alkali earth metal.]);

(VI)

(Wherein, m and n are each independently an integer of 1 to 3;

k and l are each independently 1 or 2;

j is 0 or 1; and

$A^1$, $A^2$ and $A^3$ are each independently hydrogen or one of following groups:

[wherein,

M, $M^1$ and $M^2$ are each independently an alkali metal or a nitrogen-containing organic base, and L is an alkali earth metal.];

R is a substituent of following structure:

[wherein,

B is a methyl group in 5-, 7-, or 8-position of tocopherol; m is an integer of 1 to 3, and D is —$CH_2(CH_3)$—CH— or —$CH(CH_3)$=C—]).

The abovementioned compounds of formulae (I) to (VI) have improved cutaneous moisturization and skin barrier repair capabilities, and are available under the trade names of ceramides PC104, PC102, PC107 etc.

Further, the phospholipid included in the artificial stratum corneum lipid lamellar layer contributes to the stability of ceramides and inhibits the gelation of ceramides. The phospholipid used herein may be a species of $C_{12}$-$C_{24}$ aliphatic chains which are extracted from plants, soybeans, eggs, etc., or further purified therefrom, and examples of the phospholipid include phosphatidyl choline, phosphatidyl ethanol amine, phosphatidyl serine, phosphatidyl glycerol, phosphatidyl inositol, phosphatidic acid, and a mixture thereof. Preferably, the phospholipid used herein is a mixture of a saturated lecithin and 20-99% by weight of an unsaturated lecithin in which the unsaturated lecithin corresponds to 10-99% by weight of phosphatidyl choline.

In the meantime, examples of the fatty acid included in the artificial stratum corneum lipid lamellar layer include a saturated or unsaturated $C_8$-$C_{30}$ fatty acid, and examples of the alcohol include a saturated or unsaturated $C_8$-$C_{30}$ alcohol.

In addition, examples of the cholesterol or derivative thereof include cholesterol, cholesteryl chloride, cholesteryl octanoate, cholesteryl nonanoate, cholesteryl oleyl carbonate, cholesteryl isostearyl carbonate, and a mixture thereof.

The molecular anchoring agent included in the artificial stratum corneum lipid lamellar layer plays a role in chemically combining a lipid-structure with a protein on the skin as to have the lipid-structure retained on skin for a long time. The molecular anchoring agent used herein is a compound having $C_{12}$-$C_{20}$ alkyl or alkenyl as a hydrophobic moiety and succinimidyl ester as a hydrophilic moiety, preferably oleyloxy-poly(ethylene glycol)$_n$-succinyl-N-hydroxysuccinimidyl ester, wherein n is an integer of 2 to 100, more preferably an integer of 10 to 80.

Preferably, the artificial stratum corneum lipid lamellar layer may comprise a phospholipid, a fatty acid, a cholesterol or a derivative thereof, an alcohol, and a molecular anchoring agent in amounts of 1~100 parts by weight, 1~100 parts by weight, 1~50 parts by weight, 1~50 parts by weight, and 1~50 parts by weight, respectively, based on 100 parts by weight of said ceramide. Such mixing ratio may be adjusted to form a stable lamellar structure.

As disclosed above, there exists a polymer layer disposed on the artificial stratum corneum lipid lamellar layer. The polymer layer encases the outside of the artificial stratum corneum lipid lamellar layer, which functions to enhance the stability of the multi-layered lamellar structure.

Such polymer layer may be, without limitation, one of those that cannot be easily dissolved in a solvent, e.g., water or a polar organic solvent and that can be coated uniformly on a surface of the artificial stratum corneum lipid lamellar layer, and may be a natural polymer, synthetic polymer, or a mixed type thereof.

Examples of the natural polymer constituting the polymer layer include hyaluronic acid, alginic acid, pectin, carrageenan, chondroitin sulfate, dextran sulfate, chitosan, chitin, polylysine, collagen, and fibrin.

Examples of the synthetic polymer constituting the polymer layer include polyethylene glycol-polylactic acid-polyethylene glycol (PEG-PLA-PEG), polyethylene glycol-poly(lactic-co-glycolic acid)-polyethylene glycol (PEG-PLGA-PEG), polyethylene glycol-polycaprolactone-polyethylene glycol (PEG-PCL-PEG), polyethylene-bis-(polylactic acid-acrylate), and phospho(isopropyl acrylamide-co-acrylic acid).

Further, examples of the mixed-type of the natural polymer and synthetic polymer constituting the polymer layer include phospho(isopropyl acryl amide-co-acrylic acid), alginate-g-(polyethyleneoxide-polypropyleneoxide-polyethyleneoxide (PEO-PPO-PEO)), phosopho(poly(lactic-co-glycolic acid)-co-serine), collagen-acrylate, and alginate. In addition, a biodegradable hydrophobic aliphatic polyester may be used as said polymer, and examples of it include poly-L-lactic acid, poly-D,L-glycolic acid, poly-L-lactic acid-co-glycolic acid, poly-D,L-lactic acid-co-glycolic acid, polycaprolactone, polyvalerolactone, polyhydroxy butyrate, polyhydroxyvalerate, polyorthoester, a copolymer prepared from a monomer thereof, and a mixture thereof.

Further, examples of the polymer used herein include a mixture of polystyrene, poly p- or m-methylstyrene, poly p- or m-ethylstyrene, poly p- or m-chlorostyrene, poly p- or m-chloromethylstyrene, polystyrene sulfonic acid, poly p- or m- or t-butoxystyrene, polymethyl(meth)acrylate, polyethyl(meth)acrylate, polypropyl(meth)acrylate, poly n-butyl (meth)acrylate, polyisobutyl(meth)acrylate, poly t-butyl (meth)acrylate, poly 2-ethylhexyl(meth)acrylate, poly n-octyl(meth)acrylate, polylauryl(meth)acrylate, polystearyl (meth)acrylate, poly 2-hydroxyethyl(meth)acrylate, polyethylene glycol(meth)acrylate, polyglycidyl(meth)acrylate, polydimethylaminoethyl(meth)acrylate, polydiethylaminoethyl(meth)acrylate, polyvinylacetate, polyvinylpropionate, polyvinylbutyrate, polyvinylether, polyallylbutylether, polyallylglycidylether, poly(meth)acrylic acid, unsaturated carboxylic acid such as polymaleic acid, polyalkyl(meth)acrylamide, or poly(meth)acrylnitrile, etc.

Said polymer layer may be used in an amount of 0.01 to 90% by weight based on the total amount of the multi-layered lamellar granule. When used in that amount, the multi-layered lamellar granule has improved stability and can be easily employed in an external skin application formulation without the occurrence of odd feelings.

The multi-layered lamellar granule of the present invention may be prepared by various coating methods, preferably, e.g., fluid bed coating method using a fluid bed coater.

The fluid-bed coating is described in detail hereinafter.

A nucleating agent is agitated using a fluidizing gas stream in a fluid-bed coater. Then, the nucleating agent is spray-coated with a mixture solution of an artificial stratum corneum lipid lamellar and dried to form an artificial stratum corneum lipid lamellar layer which encases the nucleating agent. At the time, any other ingredients (e.g., phospholipid, fatty acid, cholesterol or a derivative thereof, alcohol, or molecular anchoring agent) may be added to the mixture solution for spray-coating. When a phospholipid is used, each solution of ceramide and phospholipid may be prepared and spray-coated successively. To the separate solution, any other components may be further added.

In the procedure, a solvent for dissolving the artificial stratum corneum lipid lamellar mixture is preferred to be volatile and to dissolve the artificial stratum corneum lipid components.

The solvent used in the process is a compound which can dissolve the artificial stratum corneum lipid components, and examples of the solvent include linear alkanes such as hexane, heptane, octane, nonane, decane, etc.; linear or branched alcohols such as methanol, ethanol, propanol, butanol, etc.; $C_4$-$C_{10}$ alcohols such as pentanol, hexanol, heptanol, octanol, nonanol, decanol, etc.; $C_7$ or more alkyl ester such as n-hexyl acetate, 2-ethylhexyl acetate, methyl oleate, dibutyl seacate, dibutyl adipate, 2-butyl cabamate, etc.; aliphatic ketones such as methyl isobutylketone, isobutylketone, etc.; aromatic hydrocarbons such as benzene, toluene, o- or p-xylene, etc.; chlorine compounds such as methylene chloride, chloroform, carbon tetrachloride, but not limited thereto.

Preferably, the solvent may be methanol, ethanol, methylene chloride, chloroform, or acetone which easily evaporates, due to low boiling point.

The amount of solvent may be in the range of 10 to 99 parts by weight based on the total amount of the artificial stratum corneum lipid lamellar mixture. When used in the amount, the solvent can dissolve active ingredients effectively and coating efficiency increases due to short spraying time.

Next, the surface of the artificial stratum corneum lipid lamellar layer is secondly spray-coated with a polymer solution under a reduced pressure and dried to obtain a multi-layered lamellar granule of the present invention.

In the process, a solvent for dissolving a polymer is a chemical substance which is volatile and has solubility parameters similar to the selected polymer. Particular examples of the solvent are substantially same to those used for the artificial stratum corneum lipid lamellar mixture as disclosed above.

The amount of solvent may be 10 to 99 parts by weight based on 100 parts by weight of the polymer. When used in the amount, gelation of the polymer may be inhibited and the process efficiency may be increase due to short spraying time.

Figure 1:
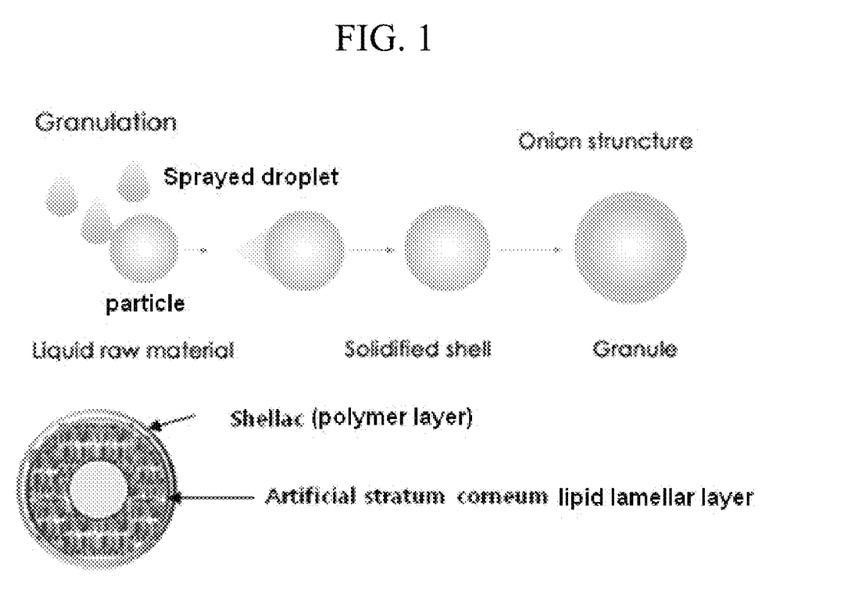
FIG. 1: a diagram showing a process of fluid bed coating and the shape of a multi-layered lamellar granule.

The abovementioned fluid-bed coating and the multi-layered lamellar granule prepared by the method are described in diagrams of FIG. 1.

Further, the present invention provides an external skin application composition comprising said multi-layered lamellar granule.

The external skin application composition of the present invention may comprise the multi-layered lamellar granule, e.g., in an amount of about 0.01 to 99% by weight, preferably in an amount of about 0.01 to 5% by weight, based on the total amount of said composition. When used in the amount, the composition has more improved formulation stability, feeling of use, skin moisturization, and barrier repair effect.

The external skin application composition of the present invention may be any kind or type of cosmetics, without special limitation, e.g., softening lotion, nourishing lotion, massage cream, nourishing cream, pack, gel, or skin-adhesive type of cosmetics. Preferably, the cosmetic composition may be oil-in-water emulsion or solubilized formulation which has improved phase stability.

The external skin application composition may be a pharmaceutical composition in which the multi-layered lamellar granule of the present invention is dispersed or dissolved in a pharmaceutically acceptable carrier, and examples are lotions, solutions, gels, creams, emollient creams, unguents, patches and sprays. The pharmaceutical composition may be used for the treatment and prevention of, for example, atopic dermatitis, miliaria, erosion, frostbite, diaper rash, contact dermatitis, seborrheic dermatitis, lichen Vidal, nummular dermatitis, housewife's eczema, photosensitivity dermatitis, insect bites, pruritus cutaneous, prurigo, drug eruption, toxic erythema, psoriasis, parapsoriasis, Pustulosis palmoplantaris, lichen planus, lichen nitidus, pityriasis rubra pilaris, Gibert pityriasis rosea, erythroplakia, dermatitis exfoliativa, dicoid lupus erythematosus, systemic lupus erythematosus, pemphigus, bollous pemphigoid, dermatitis herpetiformis Duhring, alopecia areata, vitiligo vulgaris, sarcoidosis, cutaneous amyloidosys, keloids, hypertrophic scars, wounds, bed sores, cutaneous ulcers, alopecia, and hair growth.

The external skin application composition of the present invention may also function as a base for the delivery of other therapeutic agents, and when so used, will enhance the clinical response to such agents. Examples of these other therapeutic agents are: anti-inflammatory agents (e.g., corticosteroids, colchicine, sulfasalazine, and sulfones); antibiotics (e.g., quinolones, macrolides, penicillins, cephalosporins, sulfonamides, and tetracyclines); antivirals (e.g., acyclovir, idoxuridine, zidovudine, 2',3'-dideoxyinosine (ddI), vidarabine, and trifluridine); antifungals (e.g., ketoconazole, econazole, griseofulvin, cicloprix, and naftidine); antihistamines (e.g., diphenhydramine, astemizole, hydroxyzine, doxepin, amitriptyline, cyproheptadine, and sodium cromolyn); antipruritics (e.g., camphor, menthol, phenol, benzocaine, benzyl alcohol, salicylic acid, dyclonine, and pramoxine); antineoplastic agents (e.g., methotrexate, piritrexim, cisplatin, 5-fluorouracil, bleomycin, carmustine, hydroxyurea, azathioprine, and nitrogen mustard); carboxylic acid analogs (e.g., 1-monolaurin, azelaic acid and dodecanedioic acid); natural and synthetic vitamins and analogs (e.g., vitamin D, calcipitriol, 1,25-dihydroxy cholecalciferol, retinol, retinyl palmitate, retinyl ascorbate, isotretinoin, etretinate and retinoic acid); artemisinin analogs (e.g., artesunate, arteether, artemether, dihydroartemisinin and artelenic acid).

In addition to above agents, the composition of the present invention also comprises other ingredients commonly used in a cosmetic composition or a pharmaceutical composition. Examples of the other ingredients are: lipid ingredients, humectants, emollients, emulsifiers, organic or inorganic dyes, organic powders, ultraviolet ray absorbing agents, preservatives, antiseptics, antioxidants, plant extracts, pH controllers, alcohols, pigments, perfumes, blood circulators, refrigerants, antihidrotics, and distilled water.

As explained above, the multi-layered lamellar granule comprises an artificial stratum corneum lipid lamellar layer within it, which blocks the contacts with oils and surfactants to maintain the lamellar structure similar to the stratum corneum. Accordingly, the external skin application composition of the present invention shows improved moisturization and barrier repair capabilities when applied to the skin, and may be used in cosmetics and pharmaceuticals.

The following Examples are intended to illustrate the present invention without limiting its scope.

Example 1

Preparation of Multi-Layered Lamellar Granule Comprising Artificial Stratum Corneum Lipid Lamella Layer (Pseudoceramide/Stearic Acid/Cholesterol)

Figure 2:
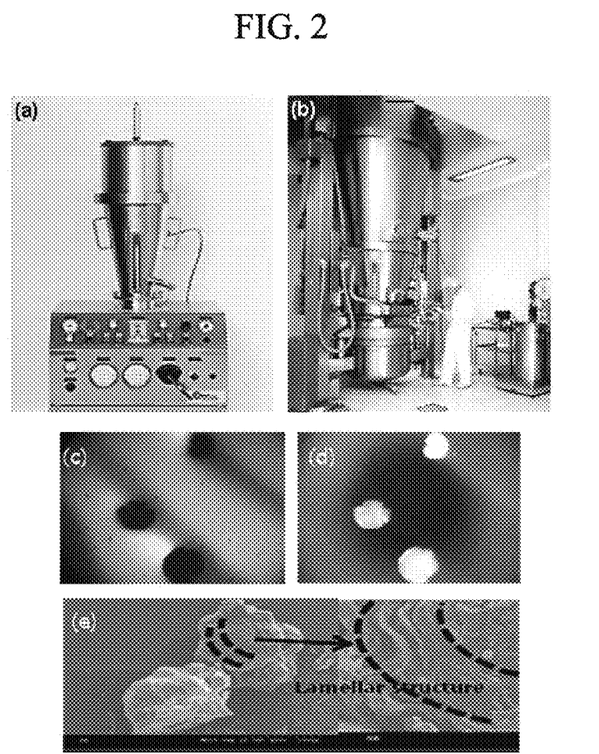
FIG. 2: photographs showing pilot-scale and production-scale of fluid bed coaters (FIGS. 2(a) and 2(b), respectively) and the granule product observed by optical microscope, polarization microscope, and electron microscope (FIGS. 2(c), 2(d), and 2(e), respectively)

A multi-layered lamellar granule was prepared using ceramide PC104 (Macrocare, Korea) as pseudoceramide, as follows:

500 g of sugar having an average particle size of 200 nm used as nucleating cores was placed in a fluid-bed coater (Glatt, Germany) and agitated using a fluidizing gas stream: A pilot-scale fluid-bed coater and a production-scale fluid-bed coater are shown in photographs of FIGS. 2(a) and (b), respectively. Subsequently, 440 g of a mixture of an artificial stratum corneum lipid lamellar was dissolved in 2000 g of ethanol. Then, the nucleating sugar particles were spray-coated with the solution at room temperature, and dried under a reduced pressure. In the above process, the solution spraying rate was 10 mL/min, and the mixture of the artificial stratum corneum lipid lamella was composed of ceramide PC104, stearic acid, and cholesterol in a weight ratio of 0.4:0.4:0.2. The surface of coated material thus obtained was spray-coated with a solution composed of 50 g of chitin and 95 g of water at a rate of 10 mL/min, and dried under a reduced pressure at room temperature. The resulting multi-layered lamellar granule was filtered through a sieve to remove minute residues and was stored in a closed pack.

Example 2

Preparation of Multi-Layered Lamellar Granule Comprising Artificial Stratum Corneum Lipid Lamella Layer (Natural Ceramide/Stearic Acid/Cholesterol)

A multi-layered lamella granule was prepared by repeating the procedure of Example 1, except for using ceramide 3 (Doosan, Korea) as a natural ceramide, instead of the pseudoceramide.

Example 3

Preparation of Multi-Layered Lamellar Granule Comprising Artificial Stratum Corneum Lipid Lamella Layer (Pseudoceramide)

A multi-layered lamella granule was prepared by repeating the procedure of Example 1, except for forming an artificial stratum corneum lipid lamella layer using only ceramide PC104 (Doosan, Korea).

Example 4

Preparation of Multi-Layered Lamellar Granule Comprising Artificial Stratum Corneum Lipid Lamella Layer (Pseudoceramide/Stearic Acid)

A multi-layered lamella granule was prepared by repeating the procedure of Example 1, except for forming an artificial stratum corneum lipid lamella layer using ceramide PC104 and stearic acid in a ratio of 1:1 by weight.

Example 5

Preparation of Multi-Layered Lamellar Granule Comprising Artificial Stratum Corneum Lipid Lamella Layer (Pseudoceramide/Palmitic Acid/Cholesterol)

A multi-layered lamella granule was prepared by repeating the procedure of Example 1, except for using palmitic acid instead of stearic acid.

Example 6

Preparation of Multi-Layered Lamellar Granule Comprising Artificial Stratum Corneum Lipid Lamella Layer (Pseudoceramide/Stearic Acid/Molecular Anchoring Agent/Phospholipid)

A multi-layered lamellar granule was prepared using ceramide PC104 (Macrocare, Korea) as pseudoceramide, as follows:

500 g of sugar having an average particle size of 200 nm used as nucleating cores was placed in a fluid-bed coater (Glatt, Germany) and agitated using a fluidizing gas stream. Subsequently, 1000 g of ceramide PC104 was dissolved in 5 kg of methylene chloride, and the nucleating sugar particles were spray-coated with the solution at room temperature and under a reduced pressure. Then, 100 g of phosphatidylcholine, 10 g of oleyloxy-poly(ethylene glycol)$_{20}$-succinyl-N-hydroxysuccinimidyl ester as a molecular anchoring agent, and 50 g of stearic acid were dissolved in 500 g of methylene chloride, and the coated material was spray-coated with the solution under the same spraying condition. Subsequently, the coated material thus obtained was further spray-coated with a solution composed of 50 g of chitin and 95 g of water. The solution spraying rate was 10 mL/min and all procedures were conducted at room temperature. The resulting multi-layered lamellar granule was filtered through a sieve to remove minute residues and was stored in a closed pack.

Example 7

Preparation of Multi-Layered Lamellar Granule Comprising Artificial Stratum Corneum Lipid Lamella Layer (Natural Ceramide/Stearic Acid/Molecular Anchoring Agent/Phospholipid)

A multi-layered lamella granule was prepared by repeating the procedure of Example 6, except for using ceramide 1 (Doosan, Korea) as a natural ceramide, instead of pseudoceramide.

Example 8

Preparation of Multi-Layered Lamellar Granule Comprising Artificial Stratum Corneum Lipid Lamella Layer (Pseudoceramide/Stearic Acid/Phospholipid)

A multi-layered lamella granule was prepared by repeating the procedure of Example 6, except for not using molecular anchoring agent.

Experimental Example 1

Structural Analysis of the Multi-Layered Lamellar Granules

Multi-layered lamellar granules prepared in Examples 1 and 2 were observed by optical microscope, polarization microscope and electron microscope: The photographs are shown in FIGS. 2(c), (d) and (e), respectively. As shown in photographs observed by polarization microscope and electron microscope, it was demonstrated that the artificial stratum corneum lipid layer of the multi-layered lamellar granule has a lamellar structure.

The lamellar granules prepared in Examples 6 and 7 (prior to forming a polymer layer) were observed by optical microscope, polarization microscope and electron microscope. The photograph of the granule obtained in Example 6, which was observed by electron microscope, was shown in FIG. 5. In case of the granule prior to forming a polymer layer, obtained in Example 6, it was confirmed that the lamellar layers are encasing the nucleating agent successively.

Figure 5:
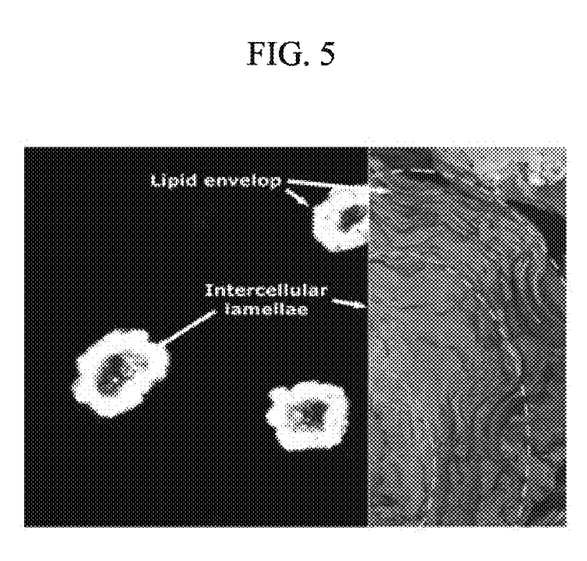
FIG. 5: an electron microscope picture of the granule prepared in Example 6.

Further, the shape of the multi-layered lamellar granule prepared in Example 7 also was same to that of FIG. 5. This indicates that ceramide, molecular anchoring agent, and fatty acid, together with phospholipid, are arranged and immobilized to a lamellar structure.

Examples 9-13 and Comparative Examples 1-3

Preparation of External Skin Application Composition

The external skin application compositions of Example 9 and Comparative Examples 1 and 2 were each formulated into an oil-in-water (O/W) emulsion using the ingredients shown in Table 1, and the external skin application compositions of Examples 10 to 13 and Comparative Example 3 into a gel using the ingredients shown in Table 2.

TABLE 1

| | Ingredient (% by weight) | Example 9 | Comparative Example 1 | Comparative Example 2 |
|---|---|---|---|---|
| Oil phase ingredients | Cetearyl alcohol | 0.5 | 0.5 | 0.5 |
| | Glyceryl stearate/PEG-100 stearate | 1.5 | 1.5 | 1.5 |
| | Cetyl octanoate | 4.0 | 4.0 | 4.0 |
| | Isopropyl palmitate | 4.0 | 4.0 | 4.0 |
| | 2-Octyl dodecanol | 4.0 | 4.0 | 4.0 |
| | Dimethicone | 1.0 | 1.0 | 1.0 |
| | Cyclomethicone | 3.0 | 3.0 | 3.0 |
| | Parahydroxybenzoic acid ester | A.A | A.A | A.A |
| | Ceramide PC104 | — | — | 0.5 |
| | Palmitic acid | — | — | 0.1 |
| | Cholesterol | — | — | 0.5 |
| | Purified water | To 100 | To 100 | To 100 |
| Aqueous phase ingredients I | Glycerin | 5.0 | 5.0 | 5.0 |
| | Butylene glycol | 5.0 | 5.0 | 5.0 |
| | Disodium EDTA | A.A | A.A | A.A |
| | TEAE | A.A | A.A | A.A |
| | Imidazolidinylurea | A.A | A.A | A.A |
| | 1% Cabomer solution | 12 | 12 | 12 |

TABLE 1-continued

| Ingredient (% by weight) | | Example 9 | Comparative Example 1 | Comparative Example 2 |
|---|---|---|---|---|
| Aqueous phase ingredients II | Multi-layered lamella granule of Example 5 | 2.0 | — | — |

● A.A denotes "an appropriate amount"

TABLE 2

| | Ingredient (% by weight) | Ex. 10 | Ex. 11 | Ex. 12 | Ex. 13 | Comp. Ex. 3 |
|---|---|---|---|---|---|---|
| Aqueous phase ingredients I | Purified water | To 100 | To 100 | To 100 | To 100 | To 100 |
| | Glycerin | 5.0 | 5.0 | 5.0 | 5.0 | 5.0 |
| | Butylene glycol | 3.0 | 3.0 | 3.0 | 3.0 | 3.0 |
| | Disodium EDTA | A.A | A.A | A.A | A.A | A.A |
| | Trehalose | 1 | 1 | 1 | 1 | 1 |
| | Hyaluronic acid | 2 | 2 | 2 | 2 | 2 |
| | PEG-75 | 1 | 1 | 1 | 1 | 1 |
| | Potassium hydroxide | A.A | A.A | A.A | A.A | A.A |
| Aqueous phase ingredient II | 1% carbomer solution | 20 | 20 | 20 | 20 | 20 |
| Aqueous phase ingredients III | Xanthan gum | 0.1 | 0.1 | 0.1 | 0.1 | 0.1 |
| | Multi-layered lamellar granule of Example 2 | 2.0 | — | — | — | — |
| | Multi-layered lamellar granule of Example 3 | — | 2.0 | — | — | — |
| | Multi-layered lamellar granule of Example 4 | — | — | 2.0 | — | — |
| | Multi-layered lamellar granule of Example 5 | — | — | — | 2.0 | — |
| Alcoholic ingredients | Ethanol 95% | 5.0 | 5.0 | 5.0 | 5.0 | 5.0 |
| | Polyoxyethylene hydrogenated caster oil | 0.3 | 0.3 | 0.3 | 0.3 | 0.3 |
| | Parahydroxybenzoic acid ester | A.A | A.A | A.A | A.A | A.A |

A.A denotes "an appropriate amount"

Preparation Method of Example 1 and Comparative Example 1

(1) The oil phase ingredients were mixed uniformly while heating at 70 to 75° C. to obtain a mixture (i);

(2) The aqueous phase ingredients I were uniformly mixed while heating at 70 to 75° C. to obtain a mixture (ii); and (3) The mixture (i) was added to the mixture (ii) while stirring at 70 to 75° C., and cooled to 28 to 30° C. to obtain an O/W emulsion. The aqueous phase ingredient II was added thereto and stirred to be homogeneously dispersed.

Experimental Example 2

Evaluation on Skin Barrier Repair Capabilities in Mice

The skin barrier repair capabilities of compositions of Examples 9-13 and Comparative Examples 1-3 were investigated as follows.

Hairless mice (Orient Bio., Korea), aged 8 to 10 weeks, were treated by repeated applications of oxazolone to the back, once a day for total 5 days, to perturb the cutaneous barrier.

The rate of transepidermal water loss (TEWL) was then measured using an evaporimeter (Delphin Co., Finland). As soon as the TEWL rates exceeded 40 g/m$^2$/h, test formulations were applied topically to the barrier-perturbed areas. Each test formulation was applied twice a day for 3 days in an amount of 50 µL per 5 cm$^2$ of skin area. Further measurements of TEWL were taken at a constant time interval, and the results were shown in FIG. 4.

Figure 4:
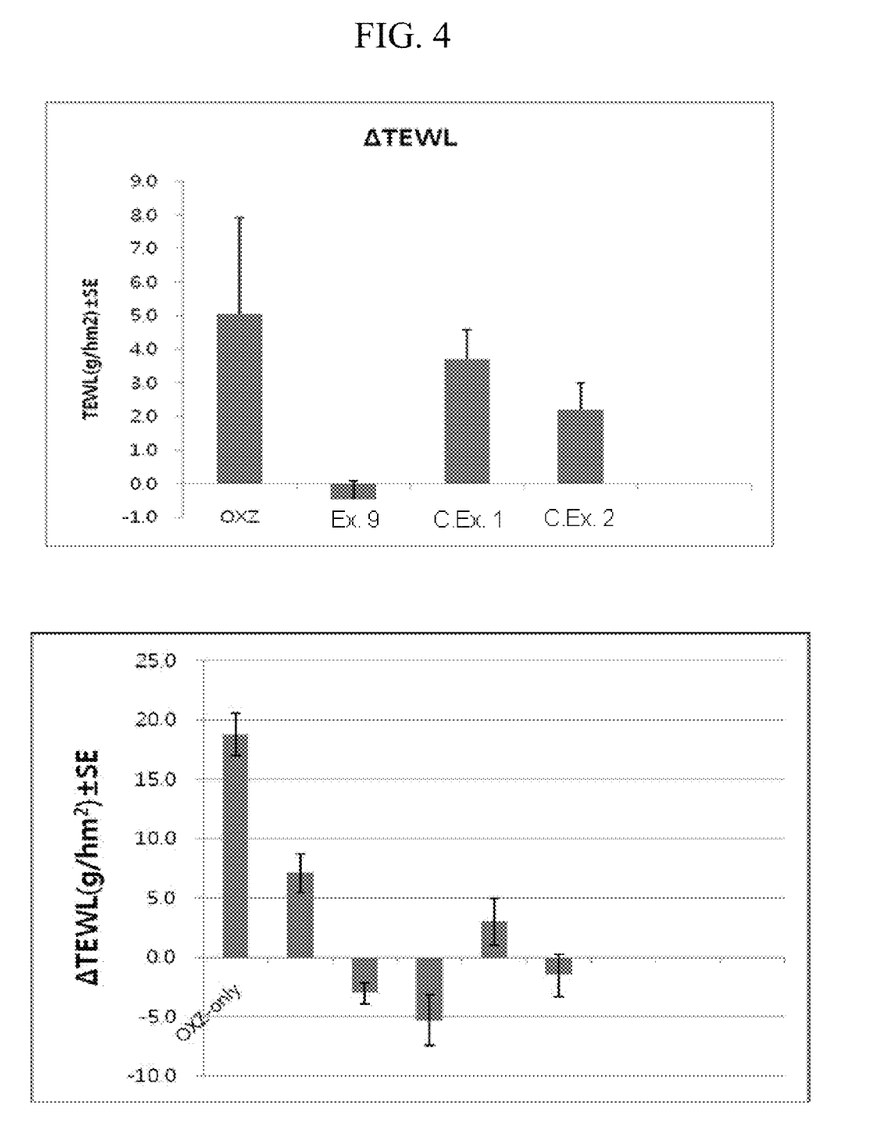
FIG. 4: the degree of the trans-epidermal water loss (TEWL) in mice having its skin barrier function disrupted (OXZ), and those observed for mice treated with the external skin application compositions of Examples 9 to 13 and Comparative Examples 1 to 3, respectively.

As shown in FIG. 4, the groups treated with the compositions of Examples 9-13 exhibited a fast barrier repair capabilities, as compared with the groups treated with the compositions of Comparative Examples 1-3.

Experimental Example 3

Evaluation of Skin Moisturizing Effect in Human

The skin moisturizing effect of oil-in-water emulsions and solubilized gels prepared in above Examples 9 and 10, and Comparative Examples 1 and 3 was measured as follows:

Forty male and female adults, aged fifties to sixties, complaining about sin dryness or suspected of dry skin were divided into four groups, and subjects of each group were treated with the cosmetic compositions of Examples 9 and 10, and Comparative Examples 1 and 3 on the face, twice a day, for 4 weeks. Skin's water content was measured using a corneometer, which measures the water content by measuring conductance in the epidermis, under constant-temperature, constant-humidity condition (24° C., R.H. 40%), prior to starting application, and again at 1 week, 2 weeks, 4 weeks after application of the composition, and at 2 weeks after 4-week application stops (6 weeks after application). The results are shown in Table 3 as a percentage of an increase of water content measured at predetermined intervals, relative to that measured at the start of application.

Apart from the water content measurement, subjective effect evaluation was also carried out by making the subjects to fill out a questionnaire, at the end of the test. The results were shown in Table 4.

TABLE 3

| | Increase of water content (%) | | | |
|---|---|---|---|---|
| | 1 week after application | 2 weeks after application | 3 weeks after application | 6 weeks after application |
| Example 9 | 47 | 49 | 51 | 46 |
| Example 10 | 30 | 32 | 37 | 35 |
| Comparative Example 1 | 33 | 35 | 38 | 25 |
| Comparative Example 3 | 22 | 29 | 31 | 15 |

TABLE 4

| | Result of questionnaire (number of respondents) | | | |
|---|---|---|---|---|
| | Very good | Good | Moderate | Poor |
| Example 9 | 2 | 10 | 0 | 0 |
| Example 10 | 0 | 6 | 3 | 0 |
| Comparative Example 1 | 1 | 7 | 1 | 1 |
| Comparative Example 3 | 0 | 3 | 4 | 2 |

As shown in Table 3, the groups treated with the compositions of Examples 9 and 10 showed a high water content than those treated with the compositions of Comparative Examples 1 and 3. Further, the water contents measured at 2 weeks after 4-week application stops (6 weeks after application) were similar to those measured after 1 or 2 weeks, which indicates that the inventive composition can retain water persistently, even though its application stops.

Further, as shown in Table 4, the subjects who applied the compositions of Examples 9 and 10 comprising the multilayered lamellar granule felt the improvement effect of skin dryness.

Examples 14-15 and Comparative Examples 4-5

Preparation of External Skin Application Composition (Solubilized Formulation)—Formulation Stability Test Transparent gel types (about 3,500 of viscosity) of solubilized formulations were prepared using the ingredients shown in Table 5. The viscosities were measured using a Brookfield (LVDVII+) viscometer, under 30° C. and 12 rpm. In the gel types of formulations, granules were added in amounts of 5% by weight, and a ceramide PC104 or a ceramide 1 was further added in order to compare stabilities of formulations. The formulations prepared above were stored in 25° C. oven and 45° C. oven, respectively, and each sample taken at 2 weeks, 4 weeks, and 8 weeks was subjected to the measurement of gelation. The results were shown in Table 6.

TABLE 5

| | Amount (% by weight) | | | |
|---|---|---|---|---|
| Ingredient | Example 14 | Example 15 | Comparative Example 4 | Comparative Example 5 |
| Glycerin | 5 | 5 | 5 | 5 |
| Propylene glycol | 4 | 4 | 4 | 4 |
| Granule of Example 6 | 5 | 5 | 5 | 5 |
| Granule of Example 7 | 0 | 5 | 0 | 0 |
| Ceramide PC104 | 0 | 0 | 3.5 | 0 |
| Ceramide 1 | 0 | 0 | 0 | 3.5 |
| Ethanol | 10 | 10 | 10 | 10 |
| Sodium polyacrylate | 0.5 | 0.5 | 0.5 | 0.5 |
| Preservative | A.A | A.A | A.A | A.A |
| Purified water | To 100 | To 100 | To 100 | To 100 |

● A.A denotes "an appropriate amount"

TABLE 6

| | Storage temperature (° C.) | After 2 weeks | After 4 weeks | After 8 weeks |
|---|---|---|---|---|
| Example 14 | 25 | X | X | X |
| | 45 | X | X | X |
| Example 15 | 25 | X | X | X |
| | 45 | X | X | X |
| Comparative Example 4 | 25 | X | X | X |
| | 45 | O | O | O |
| Comparative Example 5 | 25 | X | X | O |
| | 45 | X | O | O |

As shown in Table 6, the solubilized formulations of Examples 14 and 15 which comprise a ceramide as an artificial stratum corneum lipid lamella layer within a granule do not cause gelation. In contrast, the solubilized formulations of Comparative Examples 4 and 5 which comprise a non-granulated ceramide were gelated with time Examples 16-18 and Comparative Examples 6-7

Preparation of External Skin Application Composition (Emulsified Formulation)—Formulation Stability Test To investigate the inhibitory effect of gelation in an emulsified formulation, lotions were prepared using the ingredients shown in Table 7. Oil phase ingredients and aqueous phase ingredients were dispersed completely at 70° C., respectively, and emulsified at 7,000 rpm for 5 minutes to prepare opaque gel types of lotions. The viscosities of the lotions were about 3,000 cps. The formulations prepared above were stored in 25° C. oven and 45° C. oven, respectively, and each sample taken at 2 weeks, 4 weeks, and 8 weeks was subjected to the measurement of gelation. The results were shown in Table 8.

TABLE 7

| | Amount (% by weight) | | | | |
|---|---|---|---|---|---|
| Ingredient | Example 16 | Example 17 | Comparative Example 6 | Comparative Example 7 | Example 18 |
| Stearic acid | 2 | 2 | 2 | 2 | 2 |
| Cetyl alcohol | 2 | 2 | 2 | 2 | 2 |
| Lanoline alcohol | 2 | 2 | 2 | 2 | 2 |
| Liquefied paraffin | 7 | 7 | 7 | 7 | 7 |

TABLE 7-continued

| Ingredient | Amount (% by weight) | | | | |
|---|---|---|---|---|---|
| | Example 16 | Example 17 | Comparative Example 6 | Comparative Example 7 | Example 18 |
| Cyclomethicone | 5 | 5 | 5 | 5 | 5 |
| Polyoxyethylene monooleic acid ester | 2 | 2 | 2 | 2 | 2 |
| Preservative, antioxidant | A.A | A.A | A.A | A.A | A.A |
| Glycerin | 3 | 3 | 3 | 3 | 3 |
| Propylene glycol | 5 | 5 | 5 | 5 | 5 |
| Triethylamine | 1 | 1 | 1 | 1 | 1 |
| Sodium polyacrylate | 0.15 | 0.15 | 0.15 | 0.15 | 0.15 |
| Granule of Example 6 | 5 | 0 | 0 | 0 | 0 |
| Granule of Example 7 | 0 | 5 | 0 | 0 | 0 |
| Granule of Example 8 | 0 | 0 | 0 | 0 | 5 |
| Ceramide PC104 | 0 | 0 | 3.5 | 0 | 0 |
| Ceramide 1 | 0 | 0 | 0 | 3.5 | 0 |
| Purified water | To 100 | To 100 | To 100 | To 100 | To 100 |

● A.A denotes "an appropriate amount"

TABLE 8

| | Storage temperature | After 4 weeks | After 8 weeks | After 16 weeks |
|---|---|---|---|---|
| Example 16 | 25 | X | X | X |
| | 45 | X | X | X |
| Example 17 | 25 | X | X | X |
| | 45 | X | X | X |
| Comparative Example 6 | 25 | X | X | X |
| | 45 | O | O | O |
| Comparative Example 7 | 25 | X | X | O |
| | 45 | X | O | O |

As shown in Table 8, the emulsified formulations of Examples 16 and 17 which comprise a ceramide as an artificial stratum corneum lipid lamella layer within a granule do not cause gelation. In contrast, the emulsified formulations of Comparative Examples 6 and 7 which comprise a non-granulated ceramide were gelated with time Reference Example 1

Ration Determination of Artificial Stratum Corneum Lipid Lamellar Mixture

Figure 3:
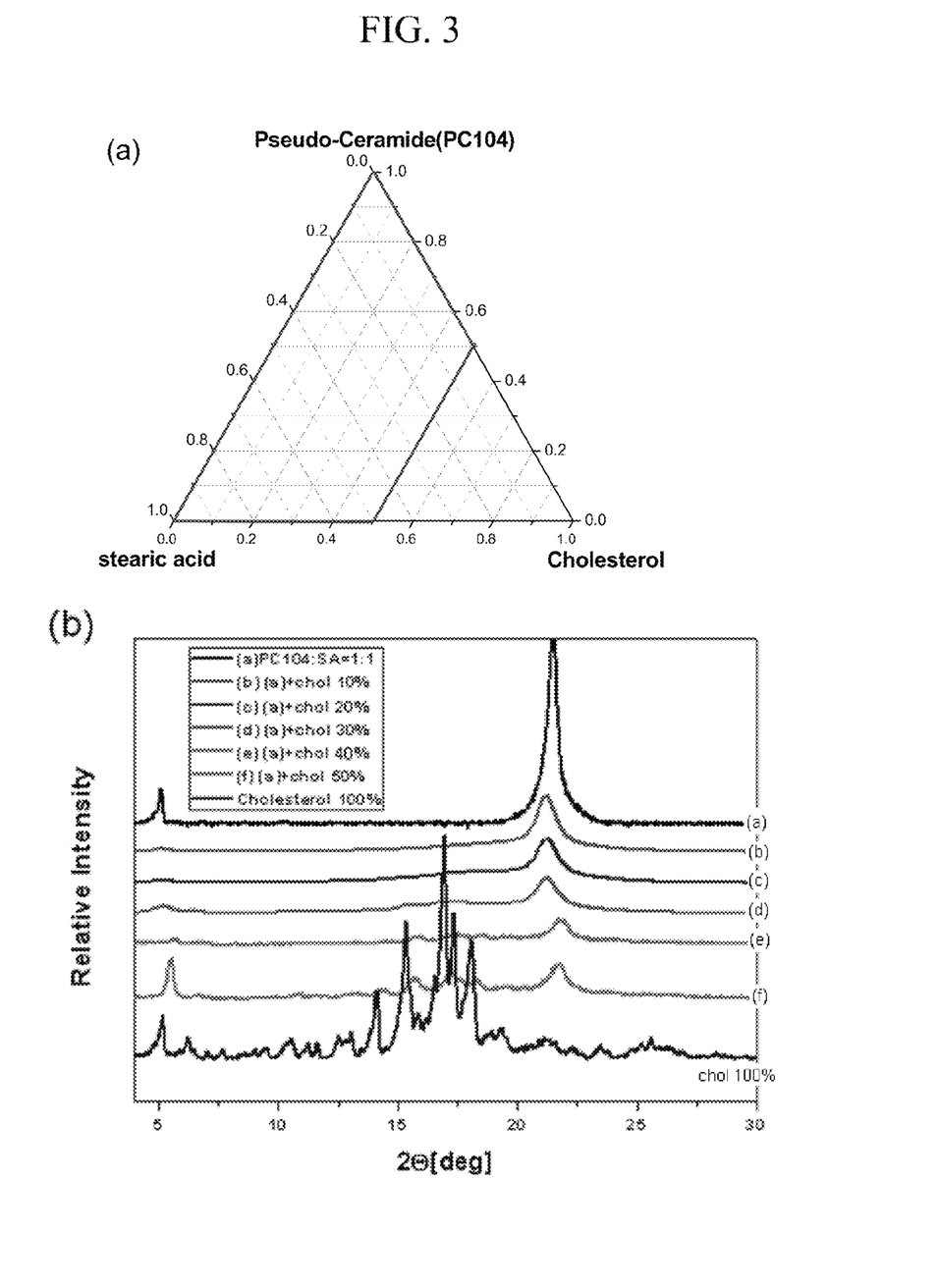
FIG. 3: a diagram of the region for a specific tertiary system composed of a ceramide PC104, a stearic acid and a cholesterol (FIG. 3(a)) and various X-ray diffraction scans thereof (FIG. 3(b))

Using an artificial stratum corneum lipid lamellar mixture consisting of ceramide PC104, stearic acid, and cholesterol as a tertiary system, an optimum ratio of the ingredients, in which the mixture has a lamellar structure similar to the skin stratum corneum, was determined as follows. As shown in FIG. 3, three ingredients were each divided into ten of concentrations in the range of 0 to 1% by weight, and were mixed each other. Then, each mixture was dissolved at 70° C. and stored at 70° C. for 4 months to analyze the change of lamellar structure. The result shows that composition of the mixture having an artificial stratum corneum layer is present in a tertiary system of the region of 0-1.0% by weight of ceramide, 0-1.0% by weight of stearic acid, and 0-0.5% by weight of cholesterol.

As shown in XRD analysis of FIG. 3, most stable lamellar shape was formed in a weight ratio of ceramide PC104, stearic acid, and cholesterol of 0.4:0.4:0.2.

Reference Example 2

Effect of Molecular Anchoring Agent

To verify effects of a molecular anchoring agent in a multi-layered lamellar granule, the following test was conducted.

Figure 6:
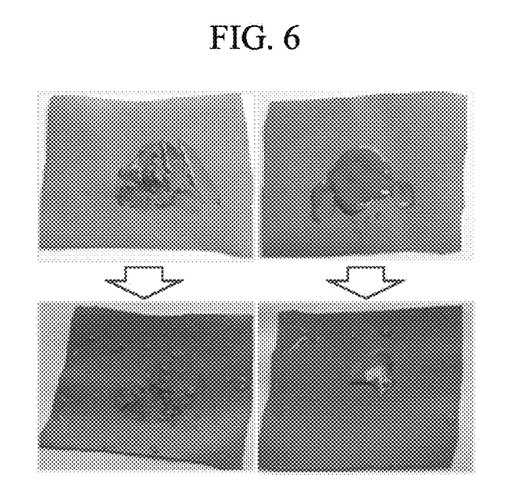
FIG. 6: the amount of absorbed pigment observed after applying a mixture of the external skin application composition of Example 16 or Example 18 and a pigment on an artificial skin (left: Example 16, right: Example 18).

0.2 g of the emulsified formulations prepared in Examples 16 and 18 were each applied onto an artificial skin, 0.01 g of 1/1000 dilution solution of soluble pigment, Red color No. 227 was added thereto and mixed well. Then, the artificial skin was washed with 1000 mL of water for 7 min, by magnetic stirring, the amount of absorbed pigment was observed. The results were shown in photographs of FIG. 6 (left: formulation of Example 16, right: formulation of Example 18). As shown in FIG. 6, the formulation of Example 16 comprising a molecular anchoring agent remained on the skin mostly. In contrast, the formulation of Example 18 without a molecular anchoring agent was significantly washed out. This indicates that the multi-layered lamellar granule can be present on the skin for more long time using a molecular anchoring agent.

While the invention has been described with respect to the above specific embodiments, it should be recognized that various modifications and changes may be made and also fall within the scope of the invention as defined by the claims that follow.

What is claimed is:

1. A multi-layered lamellar granule comprising:
   a nucleating agent particle; and
   a ceramide-containing artificial stratum corneum lipid layer, said artificial stratum corneum lipid layer having a multi-layered lamellar structure that is spray-coated on the nucleating agent particle and embeds the nucleating agent particle in the multi-layered lamellar structure,
   wherein an outer surface of the multi-layered lamellar granule of the artificial stratum corneum lipid lamellar layer and the nucleating agent particle is spray-coated with a polymer layer; and
   wherein the nucleating agent particle is a particle made of the substance selected from the group consisting of sugar, a salt, hyaluronic acid, alginic acid, chondroitin sulfate, chitosan, chitin, polylysine, collagen, gelatin, stearic acid, cetyl alcohol, stearyl alcohol, and a mixture thereof.

2. The multi-layered lamellar granule of claim 1, wherein the amount of the nucleating agent is 1 to 99% by weight based on the total amount of the multi-layered lamellar granule.

3. The multi-layered lamellar granule of claim 1, wherein the ceramide is a natural ceramide, a pseudoceramide, or a mixture thereof.

4. The multi-layered lamellar granule of claim 3, wherein the natural ceramide is selected from the group consisting of ceramide 1, ceramide 2, ceramide 3, ceramide 4, ceramide 5, ceramide 6, ceramide 7, ceramide 8, and a mixture thereof.

5. The multi-layered lamellar granule of claim 3, wherein the pseudoceramide is selected from the group consisting of compounds of formulae (I) to (VI), and a mixture thereof:

(I)

wherein,

R is a saturated or unsaturated $C_9$-$C_{21}$ aliphatic chain moiety;

(II)

wherein, n is 1 or 2; and

R and R' are each a saturated or unsaturated $C_9$-$C_{21}$ aliphatic chain moiety;

(III)

wherein, m and n are each independently an integer of 1 to 3;

k and l are each independently 1 or 2;

j is 0 or 1;

R and R' are each independently a linear or branched, saturated or unsaturated $C_1$-$C_{31}$ hydrocarbon group, optionally having one or more hydroxyl substituents; and $A^1$, $A^2$ and $A^3$ are each independently hydrogen or one of following groups, with the proviso that $A^1$, $A^2$ and $A^3$ are not simultaneously hydrogen:

wherein, M, $M^1$ and $M^2$ are each independently selected from the group consisting of an alkali metal, a lysine moiety, an arginine moiety, a histidine moiety, triethylammonium, ammonium, polyquaternium-4, polyquaternium-6, polyquaternium-7, polyquaternium-10, polyquaternium-11, polyquaternium-16, lauryldimethylbenzylammoniumchloride and stearyldimethylbenzylammoniumchloride, and L is an alkali earth metal;

(IV)

wherein,

R and R' are each independently a linear or branched, saturated or unsaturated $C_{10}$-$C_{32}$ hydrocarbon group, optionally having one or more hydroxyl substituents;

$R^3$ and $R^4$ are each independently hydrogen, $C_1$-$C_4$ alkyl, or $C_1$-$C_4$ hydroxyl alkyl; and $R^5$ is -A or —$CH_2CH_2OA$, wherein A is one of following groups;

wherein, M, $M^1$ and $M^2$ are each independently selected from the group consisting of an alkali metal, a lysine moiety, an arginine moiety, a histidine moiety, triethylammonium, ammonium, polyquaternium-4, polyquaternium-6, polyquaternium-7, polyquaternium-10, polyquaternium-11, polyquaternium-16, lauryldimethylbenzylammoniumchloride and stearyldimethylbenzylammoniumchloride, and L is an alkali earth metal;

(V)

wherein, m and n are each independently an integer of 1 to 4;

R and R' are each independently a linear or branched, saturated or unsaturated $C_1$-$C_{31}$ hydrocarbon group, optionally having one or more hydroxyl substituents;

$A_1$ and $A_2$ are each independently hydrogen or one of following groups:

wherein, M, $M^1$ and $M^2$ are each independently an alkali metal or a nitrogen-containing organic base, and L is an alkali earth metal;

(VI)

wherein, m and n are each independently an integer of 1 to 3;

k and l are each independently 1 or 2;

j is 0 or 1; and $A^1$, $A^2$ and $A^3$ are each independently hydrogen or one of following groups:

wherein, M, $M^1$ and $M^2$ are each independently an alkali metal or a nitrogen-containing organic base, and L is an alkali earth metal;

R is a substituent of following structure:

wherein, B is a methyl group in 5-, 7-, or 8-position of tocopherol; m is an integer of 1 to 3, and D is —$CH_2$($CH_3$)—CH— or —CH($CH_3$)=C.

6. The multi-layered lamellar granule of claim 1, wherein the amount of the artificial stratum corneum lipid lamellar layer is 0.00001 to 99% by weight based on the total amount of the multi-layered lamellar granule.

7. The multi-layered lamellar granule of claim 1, wherein the artificial stratum corneum lipid lamellar layer further comprises a phospholipid, a fatty acid, a cholesterol or a derivative thereof, an alcohol, a molecular anchoring agent, or a mixture thereof.

8. The multi-layered lamellar granule of claim 7, wherein the phospholipid is selected from the group consisting of phosphatidyl choline, phosphatidyl ethanolamine, phosphatidyl serine, phosphatidyl glycerol, phosphatidyl inositol, phosphatidic acid, and a mixture thereof.

9. The multi-layered lamellar granule of claim 7, wherein the fatty acid is a saturated or an unsaturated $C_8$-$C_{30}$ fatty acid.

10. The multi-layered lamellar granule of claim 7, wherein the cholesterol or a derivative thereof is selected from the group consisting of cholesterol, cholesteryl chloride, cholesteryl octanoate, cholesteryl nonanoate, cholesteryl oleyl carbonate, cholesteryl isostearyl carbonate, and a mixture thereof.

11. The multi-layered lamellar granule of claim 7, wherein the alcohol is a saturated or an unsaturated $C_8$-$C_{30}$ alcohol.

12. The multi-layered lamellar granule of claim 7, wherein the molecular anchoring agent has a $C_{12}$-$C_{20}$ alkyl or alkenyl group as a hydrophobic moiety and a succinimidyl ester group as a hydrophilic moiety.

13. The multi-layered lamellar granule of claim 12, wherein the molecular anchoring agent is an oleyloxy-poly(ethylene glycol)$_n$-succinyl-N-hydroxysuccinimidyl ester, wherein n is an integer of 2 to 100.

14. The multi-layered lamellar granule of claim 7, wherein the amount of the phospholipid, fatty acid, cholesterol or derivative thereof, alcohol, and molecular anchoring agent is 1-100 parts by weight, 1-100 parts by weight, 1-50 parts by weight, 1-50 parts by weight, and 1-50 parts by weight, respectively, based on 100 parts by weight of ceramide.

15. The multi-layered lamellar granule of claim 1, wherein the amount of the polymer layer is 0.01 to 90% by weight based on the total amount of the multi-layered lamellar granule.

16. The multi-layered lamellar granule of claim 1, wherein the multi-layered lamellar granule is prepared using a fluid-bed coater.

17. An external skin application composition comprising the multi-layered lamellar granule of claim 1.

18. The composition of claim 17, wherein the amount of the multi-layered lamellar granule is 0.01 to 99% by weight based on the total amount of the composition.

19. The composition of claim 17, wherein the composition is a cosmetic composition or a pharmaceutical composition.

* * * * *